United States Patent
Chen et al.

(10) Patent No.: US 10,650,234 B2
(45) Date of Patent: May 12, 2020

(54) EYEBALL MOVEMENT CAPTURING METHOD AND DEVICE, AND STORAGE MEDIUM

(71) Applicant: Ping An Technology (Shenzhen) Co., Ltd., Shenzhen, Guangdong (CN)

(72) Inventors: Lin Chen, Guangdong (CN); Guohui Zhang, Guangdong (CN)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 16/338,456

(22) PCT Filed: Oct. 31, 2017

(86) PCT No.: PCT/CN2017/108746
§ 371 (c)(1),
(2) Date: Mar. 29, 2019

(87) PCT Pub. No.: WO2019/033567
PCT Pub. Date: Feb. 21, 2019

(65) Prior Publication Data
US 2020/0042788 A1    Feb. 6, 2020

(30) Foreign Application Priority Data
Aug. 17, 2017  (CN) .......................... 2017 1 0708372

(51) Int. Cl.
*G06K 9/00* (2006.01)
*A61B 3/00* (2006.01)
(Continued)

(52) U.S. Cl.
CPC ........ *G06K 9/00604* (2013.01); *A61B 3/0025* (2013.01); *A61B 3/113* (2013.01); *G02B 27/0093* (2013.01); *G06K 9/00281* (2013.01)

(58) Field of Classification Search
CPC .. G06K 9/00604; G06K 9/00281; G06K 9/00; A61B 3/0025; A61B 3/113; G02B 27/0093
(Continued)

(56) References Cited

U.S. PATENT DOCUMENTS

| 8,396,282 B1 * | 3/2013 | Huber | G06K 9/629 |
| | | | 381/56 |
| 2006/0270945 A1 * | 11/2006 | Ghajar | A61B 5/163 |
| | | | 600/558 |

(Continued)

FOREIGN PATENT DOCUMENTS

| CN | 101383001 A | 3/2009 |
| CN | 104123543 A | 10/2014 |

(Continued)

OTHER PUBLICATIONS

First Office Action of Counterpart Chinese Patent Application No. 201710708372.3 dated May 31, 2018.
(Continued)

*Primary Examiner* — Jerome Grant, II

(57) ABSTRACT

The application discloses an eyeball movement capturing method, which includes: acquiring a real-time image shot by a photographic device and extracting a real-time facial image; inputting the real-time facial image into a pretrained eyeball mean shape and recognizing $n_1$ orbit feature points and $n_2$ eyeball feature points; and calculating a movement direction and movement distance of an eyeball in the real-time facial image according to x and y coordinates of the $(n_1+n_2)$ eyeball feature points in the real-time facial image. The application also discloses an electronic device and a computer-readable storage medium. According to the application, movement information of the eyeball in the real-time facial image is calculated according to the coordinates of the
(Continued)

Calculating a center coordinate of an orbit in the real-time facial image according to the x and y coordinates of the $n_1$ orbit feature points — S31

Calculating a positional relationship between a center of the orbit and each eyeball feature point to judge the movement direction and movement distance of the eyeball — S32 eye feature points to implement real-time capturing of an eyeball movement.

17 Claims, 4 Drawing Sheets

(51) Int. Cl.
*A61B 3/113* (2006.01)
*G02B 27/00* (2006.01)

(58) Field of Classification Search
USPC .......................................................... 382/103
See application file for complete search history.

(56) References Cited

U.S. PATENT DOCUMENTS

| | | | | |
|---|---|---|---|---|
| 2014/0154651 A1* | 6/2014 | Stack | ....................... | A61B 5/16 434/236 |
| 2016/0063303 A1* | 3/2016 | Cheung | .................. | A61B 3/113 382/103 |
| 2017/0023793 A1* | 1/2017 | Shtukater | ........... | G02B 27/0179 |
| 2017/0053165 A1* | 2/2017 | Kaehler | ................ | G02B 27/017 |
| 2017/0205876 A1* | 7/2017 | Vidal | ....................... | G01S 17/88 |
| 2017/0270636 A1* | 9/2017 | Shtukater | ................... | G06T 3/20 |
| 2018/0039846 A1* | 2/2018 | Grubb | ................ | G06K 9/00845 |
| 2018/0074581 A1* | 3/2018 | Melman | .................. | G06F 3/013 |

FOREIGN PATENT DOCUMENTS

| | | |
|---|---|---|
| CN | 104866105 A | 8/2015 |
| CN | 105141938 A | 12/2015 |
| CN | 105930821 A | 9/2016 |
| CN | 106527705 A | 3/2017 |
| JP | 2014194617 A | 10/2014 |

OTHER PUBLICATIONS

International Search Report of PCT Patent Application No. PCT/CN2017/108746 dated May 21, 2018.

1st Office Action of counterpart Chinese Patent Application No. 201710708372.3 dated May 31, 2018.

Notification to Grant Patent Right of counterpart Chinese Patent Application No. 201710708372.3 dated Jul. 16, 2018.

* cited by examiner

//EYEBALL MOVEMENT CAPTURING METHOD AND DEVICE, AND STORAGE MEDIUM

CLAIM OF PRIORITY

This application is based on the Paris Convention and claims priority to China Patent Application No. CN201710708372.3, filed on Aug. 17, 2017 and entitled "Eyeball Movement Capturing Method and Device, and Storage Medium", which is hereby incorporated by reference in its entirety.

TECHNICAL FIELD

The application relates generally to the technical field of computer vision processing, and particularly relates to an eyeball movement capturing method and device, and a computer-readable storage medium.

BACKGROUND

Eyeball movement capturing is a biological recognition technology for recognizing an eye movement of a user on the basis of facial feature information of the user. At present, eyeball movement capturing is applied to extensive fields, plays a very important role in many fields of financial payment, access control and attendance, identity recognition and the like and brings great convenience to people's lives. For a product, a method is usually to detect an electric field change about an eyeball by use of professional equipment so as to capture the eyeball or to recognize a change in an iris angle by use of camera equipment to track the eyeball.

However, the above two methods both have shortcomings. For the first method, the professional equipment is required to be worn and there is a strict requirement on an environment. For the second method, during iris detection, a human eye is required to be relatively close to a camera and the method is low in iris detection speed and unsuitable for a real-time condition.

SUMMARY

The application provides an eyeball movement capturing method and device and a computer-readable storage medium, which mainly aim at calculating movement information of an eyeball in a real-time facial image according to a coordinate of an eye feature point to implement real-time capturing of an eyeball movement.

In order to achieve the foregoing objective, the application provides an electronic device, which includes a memory, a processor and a photographic device, the memory including an eyeball movement capturing program and the eyeball movement capturing program being executed by the processor to implement the following steps of:

a real-time facial image acquisition step: acquiring a real-time image shot by the photographic device and extracting a real-time facial image from the real-time image by use of a face recognition algorithm;

a feature point recognition step: inputting the real-time facial image into a pretrained eye mean shape and recognizing $n_1$ orbit feature points and $n_2$ eyeball feature points representative of an eye position in the real-time facial image by use of the eye mean shape; and an eyeball position calculation step: calculating a movement direction and movement distance of an eyeball in the real-time facial image according to x and y coordinates of the $n_1$ orbit feature points and $n_2$ eyeball feature points in the real-time facial image.

Preferably, the eyeball position calculation step includes:

calculating a center coordinate of an orbit in the real-time facial image according to the x and y coordinates of the $n_1$ orbit feature points; and calculating a positional relationship between a center of the orbit and each eyeball feature point to judge the movement direction and movement distance of the eyeball.

Preferably, the feature point recognition step further includes:

aligning the real-time facial image and the eye mean shape and searching the real-time facial image for the $n_1$ orbit feature points and $n_2$ eyeball feature points matched with $n_1$ orbit feature points and $n_2$ eyeball feature points of the eye mean shape by use of a feature extraction algorithm.

Preferably, training steps for the eye mean shape include:

a feature vector sample extraction step: establishing a sample library with n facial images and marking $n_1$ orbit feature points and $n_2$ eyeball feature points in each facial image in the sample library, the $(n_1+n_2)$ feature points in each facial image forming a shape feature vector S to obtain n shape feature vectors S of an eye; and a model training step: training a facial feature recognition model by use of the n shape feature vectors S to obtain the eye mean shape about faces.

In addition, in order to achieve the foregoing objective, the application also provides an eyeball movement capturing method, which includes:

a real-time facial image acquisition step: acquiring a real-time image shot by a photographic device and extracting a real-time facial image from the real-time image by use of a face recognition algorithm;

a feature point recognition step: inputting the real-time facial image into a pretrained eye mean shape and recognizing $n_1$ orbit feature points and $n_2$ eyeball feature points representative of an eye position in the real-time facial image by use of the eye mean shape; and an eyeball position calculation step: calculating a movement direction and movement distance of an eyeball in the real-time facial image according to x and y coordinates of the $n_1$ orbit feature points and $n_2$ eyeball feature points in the real-time facial image.

Preferably, the eyeball position calculation step includes:

calculating a center coordinate of an orbit in the real-time facial image according to the x and y coordinates of the $n_1$ orbit feature points; and calculating a positional relationship between a center of the orbit and each eyeball feature point to judge the movement direction and movement distance of the eyeball.

Preferably, the feature point recognition step further includes:

aligning the real-time facial image and the eye mean shape and searching the real-time facial image for the $n_1$ orbit feature points and $n_2$ eyeball feature points matched with $n_1$ orbit feature points and $n_2$ eyeball feature points of the eye mean shape by use of a feature extraction algorithm.

Preferably, training steps for the eye mean shape include:

a feature vector sample extraction step: establishing a sample library with n facial images and marking $n_1$ orbit feature points and $n_2$ eyeball feature points in each facial image in the sample library, the $(n_1+n_2)$ feature points in each facial image forming a shape feature vector S to obtain n shape feature vectors S of an eye; and a model training step: training a facial feature recognition model by use of the n shape feature vectors S to obtain the eye mean shape about faces.

Preferably, the facial feature recognition model is an ensemble of regression trees (ERT) algorithm and is represented by a formula as follows:

$$\hat{S}^{t+1} = \hat{S}^t + \tau_t(I, \hat{S}^t),$$

where t represents a concatenation sequence number, $\tau_t(\cdot,\cdot)$ represents a regressor of a present stage and S(t) is a shape estimate of a present model; each regressor $\tau_t(\cdot,\cdot)$ predicts an increment $\tau_t(I,\hat{S}^t)$ according to an input present image I and S(t); and in a model training process, part of feature points of all sample pictures are extracted to train a first regression tree, a second tree is trained by use of residuals between predicted values of the first regression tree and true values of the part of feature points, and so on, when predicted values of an Nth trained tree and the true values of the part of feature points are close to zero, all regression trees of the ERT algorithm are obtained, and the eye mean shape for the faces is obtained according to these regression trees.

Moreover, in order to achieve the foregoing objective, the application also provides a computer-readable storage medium, which includes an eyeball movement capturing program, the eyeball movement capturing program being executed by a processor to implement any step in the foregoing eyeball movement capturing method.

According to the eyeball movement capturing method and device and computer-readable storage medium disclosed in the application, the real-time facial image is input into the eye mean shape, the orbit feature points and eyeball feature points in the real-time facial image are recognized by use of the eye mean shape and movement information of the eyeball in the real-time facial image is calculated according to the coordinates of the orbit feature points and the eyeball feature points to implement real-time capturing of an eyeball movement.

BRIEF DESCRIPTION OF THE ACCOMPANYING DRAWINGS

Achievement of the objective, functional characteristics and advantages of the application will further be described in combination with embodiments and with reference to the accompanying drawings.

DETAILED DESCRIPTION OF ILLUSTRATED EMBODIMENTS

It is to be understood that the specific embodiments described herein are adopted not to limit the application but only to explain the application.

Figure 1:
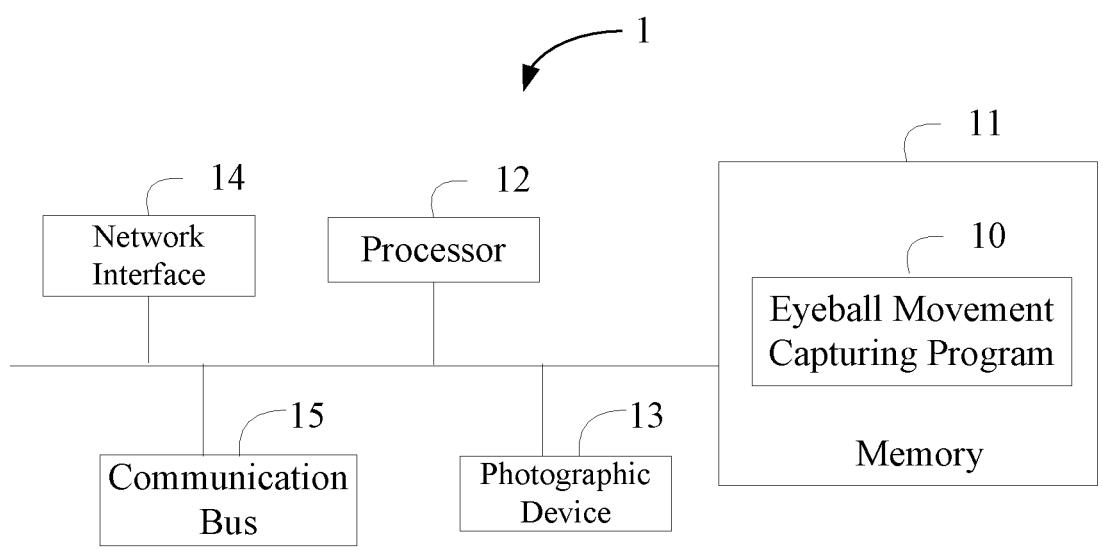
FIG. 1 is a schematic diagram of a preferred embodiment of an electronic device according to the application.

The application provides an electronic device 1. FIG. 1 is a schematic diagram of a preferred embodiment of an electronic device 1 according to the application.

In the embodiment, the electronic device 1 may be terminal equipment with an operation function such as a server, a smart phone, a tablet computer, a portable computer and a desktop computer.

The electronic device 1 includes a processor 12, a memory 11, a photographic device 13, a network interface 14 and a communication bus 15. Herein, the photographic device 13 is mounted at a specific place, for example, an office place and a monitoring region, shoots a target entering the specific place in real time to obtain a real-time image and transmits the shot real-time image to the processor 12 through a network. The network interface 14 may optionally include a standard wired interface and wireless interface (for example, wireless-fidelity (WI-FI) interface). The communication bus 15 is configured to implement connection and communication between these components.

The memory 11 includes at least one type of readable storage medium. The at least one type of readable storage medium may be a nonvolatile storage medium such as a flash memory, a hard disk, a multimedia card and a card type memory 11. In some embodiments, the readable storage medium may be an internal storage unit of the electronic device 1, for example, a hard disk of the electronic device 1. In some other embodiments, the readable storage medium may also be an external memory 11 of the electronic device 1, for example, a plug-in type hard disk, smart media card (SMC), secure digital (SD) card and flash card configured on the electronic device 1.

In the embodiment, the readable storage medium of the memory 11 is usually configured to store an eyeball movement capturing program 10 installed in the electronic device 1, a facial image sample library, a constructed and trained eye mean shape and the like. The memory 11 may further be configured to temporally store data which has been output or is to be output.

In some embodiments, the processor 12 may be a central processing unit (CPU), a microprocessor or another data processing chip and is configured to run a program code stored in the memory 11 or process data, for example, executing the eyeball movement capturing program 10.

FIG. 1 only illustrates the electronic device 1 with the components 11-15 and the eyeball movement capturing program 10. However, it is to be understood that not all of the illustrated components are required to be implemented and, instead, more or fewer components may be implemented.

Optionally, the electronic device 1 may further include a user interface. The user interface may include an input unit such as a keyboard, a voice input device such as equipment with a voice recognition function like a microphone and a voice output device such as a sound and an earphone. Optionally, the user interface may also include a standard wired interface and wireless interface.

Optionally, the electronic device 1 may further include a display. The display may also be properly called a display screen or a display unit, and in some embodiments, may be a light-emitting diode (LED) display, a liquid crystal display, a touch liquid crystal display, an organic light-emitting diode (OLED) touch device and the like. The display is configured to display information processed in the electronic device 1 and configured to display a visual user interface.

Optionally, the electronic device 1 further includes a touch sensor. A region provided by the touch sensor for a touch operation of a user is called a touch region. In addition, the touch sensor may be a resistive touch sensor, a capacitive touch sensor and the like. Moreover, the touch sensor not only includes a contact type touch sensor and but also may include a proximity touch sensor and the like. Besides, the touch sensor may be a single sensor and may also be multiple sensors arranged in, for example, an array.

Furthermore, an area of the display of the electronic device 1 and an area of the touch sensor may be the same and may also be different. Optionally, the display and the touch sensor are arranged in a stacking manner to form a touch display screen. The device senses the touch operation triggered by the user on the basis of the touch display screen.

Optionally, the electronic device 1 may further include a Radio Frequency (RF) circuit, a sensor, an audio circuit and the like. No more elaborations will be made herein.

In the device embodiment shown in FIG. 1, the memory 11 used as a computer storage medium may include an operating system and the eyeball movement capturing program 10. The processor 12 executes the eyeball movement capturing program 10 stored in the memory 11 to implement the following steps.

A real-time facial image acquisition step: a real-time image shot by the photographic device 13 is acquired, and a real-time facial image is extracted from the real-time image by use of a face recognition algorithm.

When the photographic device 13 shoots the real-time image, the photographic device 13 sends the real-time image to the processor 12. After the processor 12 receives the real-time image, a picture size is acquired at first and a grayscale image with the same size is constructed. The acquired color image is converted into the grayscale image and, meanwhile, a memory space is created. A histogram of the grayscale image is equalized to reduce an information amount of the grayscale image and increase a detection speed. Then, a training library is loaded, a face in the image is detected, an object including facial information is returned, data about a position of the face is obtained and an amount of the data is recorded. A portrait region is finally acquired and stored. In such a manner, a real-time facial image extraction process is completed.

Specifically, the face recognition algorithm for extracting the real-time facial image from the real-time image may also be a geometric-feature-based method, a local feature analysis method, an eigenface method, an elastic-model-based method, a neural network method and the like.

A feature point recognition step: the real-time facial image is input into a pretrained eye mean shape and $n_1$ orbit feature points and $n_2$ eyeball feature points representative of an eye position in the real-time facial image are recognized by use of the eye mean shape.

Training steps for the eye mean shape include that:

a sample library with n facial images is established and $n_1$ orbit feature points and $n_2$ eyeball feature points are marked in each facial image in the sample library, the ($n_1+n_2$) feature points in each facial image forming a shape feature vector S to obtain n shape feature vectors S of an eye. The orbit feature points and eyeball feature points in each facial image are manually marked.

A facial feature recognition model is trained by use of the n shape feature vectors S to obtain the eye mean shape about the faces. The facial feature recognition model is an ensemble of regression trees (ERT) algorithm. The ERT algorithm is represented by a formula as follows:

$$\hat{S}^{t+1} = \hat{S}^t + \tau_t(I, \hat{S}^t),$$

where t represents a concatenation sequence number and $\tau_t(\cdot,\cdot)$ represents a regressor of a present stage. Each regressor consists of multiple regression trees and an objective of training is to obtain these regression trees.

S(t) is a shape estimate of the present model. Each regressor $\tau_t(\cdot,\cdot)$ predicts an increment $\tau_t(I,\hat{S}^t)$ according to an input image I and S(t) and adds the increment to the present shape estimate to improve the present model. The regressors of each stage perform prediction according to the feature points. A training dataset is (I1, S1), . . . , (In, Sn), where I is the input sample image and S is a shape feature vector consisting of feature points in the sample image.

In a model training process, the number of the facial images in the sample library is n. There is made such a hypothesis that each sample picture has 7 feature points (x, y), i.e., 6 orbit feature points and 1 eyeball feature point. The feature vector is $S=(x_1^i, x_2^i, x_3^i, x_4^i, x_5^i, x_6^i, x_7^i)$, i=1, 2, 3 . . . n, $x_1 \sim x_6$ representing x coordinates of the orbit feature points and $x_7$ representing an x coordinate of the eyeball feature point. Part of feature points of all the sample pictures (for example, 4 feature points are randomly selected from the 7 feature points of each sample picture) are extracted to train a first regression tree, a second tree is trained by use of residuals between predicted values of the first regression tree and true values (weighted averages of the 4 feature points extracted from each sample picture) of the part of feature points, and so on, when predicted values of an Nth trained tree and the true values of the part of feature points are close to zero, all regression trees of the ERT algorithm are obtained, the eye mean shape about the faces is obtained according to these regression trees and a model file and the sample library are stored in the memory. Since each sample for training the model is marked with the 6 orbit feature points and the 1 eyeball feature point, the trained eye mean shape for the faces may be configured to recognize the 6 orbit feature points and 1 eyeball feature point from the facial image.

After the real-time facial image is acquired and the trained eye mean shape for faces is called from the memory, the real-time facial image is aligned with the eye mean shape and then the real-time facial image is searched for 6 orbit feature points and 1 eyeball feature point matched with 6 orbit feature points and 1 eyeball feature point of the eye mean shape by use of a feature extraction algorithm. In the embodiment, the feature extraction algorithm is a scale-invariant feature transform (SIFT) algorithm. According to the SIFT algorithm, local features of each orbit feature point and eyeball feature point are extracted from the eye mean shape, an orbit feature point and an eyeball feature point are selected as a reference feature point, and the real-time facial image is searched for a feature point with a local feature the same as or similar to that of the reference feature point (for example, a difference value of the local features of the two feature points is within a preset range). According to this principle, all of the orbit feature points and the eyeball feature points are found from the real-time facial image. In another embodiment, the feature extraction algorithm may also be a speeded up robust features (SURF) algorithm, a local binary patterns (LBP) algorithm, a histogram of oriented gradients (HOG) algorithm and the like.

An eyeball position calculation step: a movement direction and movement distance of an eyeball in the real-time facial image are calculated according to x and y coordinates of the $n_1$ orbit feature points and $n_2$ eyeball feature points in the real-time facial image.

Specifically, the eyeball position calculation step includes that:

a center coordinate of an orbit in the real-time facial image is calculated according to the x and y coordinates of the $n_1$ orbit feature points; and a positional relationship between a center of the orbit and each eyeball feature point is calculated to judge the movement direction and movement distance of the eyeball.

If there are 6 orbit feature points and 1 eyeball feature point in the eye feature points recognized from the real-time facial image, $(x_1, y_1)$, $(x_2, y_2)$, $(x_3, y_3)$, $(x_4, y_4)$, $(x_5, y_5)$ and $(x_6, y_6)$ being coordinates of the 6 orbit feature points respectively and $(x_7, y_7)$ being a coordinate of the eyeball feature point, calculation formulas for the center coordinate (X, Y) of the orbit in the real-time facial image are as follows:

$$\text{center}X=(x_1+x_2+x_3+x_4+x_5+x_6)/6, \text{ and}$$

$$\text{center}Y=(y_1+y_2+y_3+y_4+y_5+y_6)/6.$$

By use of the center coordinate (X, Y) of the orbit and the coordinate $(x_7, y_7)$ of the eyeball feature point, the positional relationship therebetween is calculated and the movement direction and movement distance of the eyeball are judged through the following calculation formulae:

$$\Delta x = x_7 - \text{center}X \text{ and } \Delta y = y_7 - \text{center}Y,$$

where values of Δx and Δy represent the movement distance of the eyeball in a certain direction (left-right and top-bottom).

For example, if Δx is larger than 0, it is indicated that the eyeball moves leftwards and, if Δx is smaller than 0, it is indicated that the eyeball moves rightwards; and if Δy is larger than 0, it is indicated that the eyeball moves upwards and, if Δy is smaller than 0, it is indicated that the eyeball moves downwards.

Similarly, when $n_2>1$, that is, there are multiple eyeball feature points in the eye mean shape, the multiple eyeball feature points may be recognized from the real-time facial image, then a mean value of the x and y coordinates of the multiple eyeball feature points is taken as a center coordinate of the eyeball and a difference value with the center coordinate of the orbit is calculated.

According to the electronic device 1 disclosed in the embodiment, the real-time facial image is extracted from the real-time image, the orbit feature points and eyeball feature points in the real-time facial image are recognized by use of the eye mean shape and movement information of the eyeball in the real-time facial image is calculated according to the coordinates of the orbit feature points and the eyeball feature points to implement real-time capturing of an eyeball movement.

Figure 2:
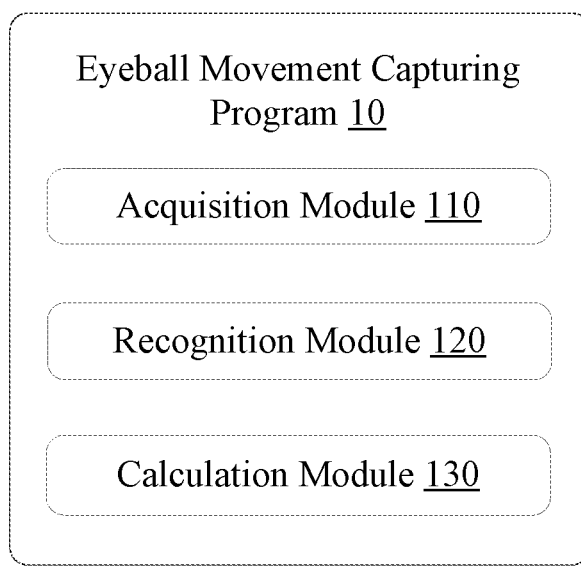
FIG. 2 is a schematic diagram of modules of an eyeball movement capturing program in FIG. 1.

In another embodiment, the eyeball movement capturing program 10 may further be divided into one or more modules and the one or more modules are stored in the memory 11 and executed by the processor 12 to implement the application. The modules in the application refer to a series of computer program instruction segments capable of realizing specific functions. FIG. 2 is a schematic diagram of modules of an eyeball movement capturing program 10 in FIG. 1. In the embodiment, the eyeball movement capturing program 10 may be divided into an acquisition module 110, a recognition module 120 and a calculation module 130. Functions or operation steps implemented by the modules 110-130 are similar to the above and will not be elaborated herein. Exemplarily, the acquisition module 110 is configured to acquire a real-time image shot by a photographic device 13 and extract a real-time facial image from the real-time image by use of a face recognition algorithm.

The recognition module 120 is configured to input the real-time facial image into a pretrained eye mean shape and recognizing $n_1$ orbit feature points and $n_2$ eyeball feature points representative of an eye position in the real-time facial image by use of the eye mean shape.

The calculation module 130 is configured to calculate a movement direction and movement distance of an eyeball in the real-time facial image according to x and y coordinates of the $n_1$ orbit feature points and $n_2$ eyeball feature points in the real-time facial image.

Figure 3:
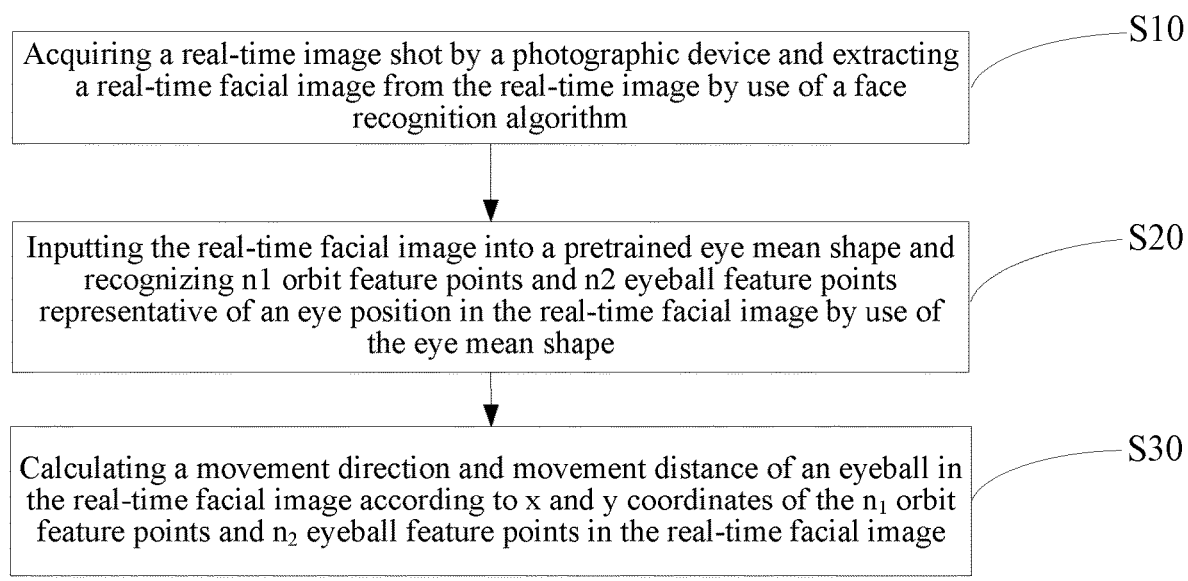
FIG. 3 is a flowchart of a preferred embodiment of an eyeball movement capturing method according to the application.

In addition, the application also provides an eyeball movement capturing method. FIG. 3 is a flowchart of a first embodiment of an eyeball movement capturing method according to the application. The method may be executed by a device and the device may be implemented by software and/or hardware.

In the embodiment, the eyeball movement capturing method includes the following steps.

In S10, a real-time image shot by a photographic device is acquired and a real-time facial image is extracted from the real-time image by use of a face recognition algorithm. When shooting the real-time image, the photographic device sends the real-time image to a processor. After the processor receives the real-time image, a picture size is acquired at first and a grayscale image with the same size is constructed. The acquired color image is converted into the grayscale image and, meanwhile, a memory space is created. A histogram of the grayscale image is equalized to reduce an information amount of the grayscale image and increase a detection speed. Then, a training library is loaded, a face in the image is detected, an object including facial information is returned, data about a position of the face is obtained and an amount of the data is recorded. A portrait region is finally acquired and stored. In such a manner, a real-time facial image extraction process is completed.

Specifically, the face recognition algorithm for extracting the real-time facial image from the real-time image may also be a geometric-feature-based method, a local feature analysis method, an eigenface method, an elastic-model-based method, a neural network method and the like.

In S20, the real-time facial image is input into a pretrained eye mean shape and $n_1$ orbit feature points and $n_2$ eyeball feature points representative of an eye position in the real-time facial image are recognized by use of the eye mean shape;

Training steps for the eye mean shape include that:

a sample library with n facial images is established and $n_1$ orbit feature points and $n_2$ eyeball feature points are marked in each facial image in the sample library, the $(n_1+n_2)$ feature points in each facial image forming a shape feature vector S to obtain n shape feature vectors S of an eye. The orbit feature points and eyeball feature points in each facial image are manually marked.

A facial feature recognition model is trained by use of the n shape feature vectors S to obtain the eye mean shape about the faces. The facial feature recognition model is an ensemble of regression trees (ERT) algorithm. The ERT algorithm is represented by a formula as follows:

$$\hat{S}^{t+1}=\hat{S}^t+\tau_t(I,\hat{S}^t)$$

where t represents a concatenation sequence number and $\tau_t(\cdot,\cdot)$ represents a regressor of a present stage. Each regressor consists of multiple regression trees and an objective of training is to obtain these regression trees.

S(t) is a shape estimate of the present model. Each regressor $\tau_t(\cdot,\cdot)$ predicts an increment $\tau_t(I,\hat{S}^t)$ according to an input image I and S(t) and adds the increment to the present shape estimate to improve the present model. The regressors of each stage perform prediction according to the feature points. A training dataset is (I1, S1), ..., (In, Sn), where I is the input sample image and S is a shape feature vector consisting of feature points in the sample image.

In a model training process, the number of the facial images in the sample library is n. There is made such a hypothesis that each sample picture has 7 feature points (x, y), i.e., 6 orbit feature points and 1 eyeball feature point. The feature vector is $S=(x_1^i, x_2^i, x_3^i, x_4^i, x_5^i, x_6^i, x_7^i)$, i=1, 2, 3 ... n, $x_1 \sim x_6$ representing x coordinates of the orbit feature points and $x_7$ representing an x coordinate of the eyeball feature point. Part of feature points of all the sample pictures (for example, 4 feature points are randomly selected from the 7 feature points of each sample picture) are extracted to train a first regression tree, a second tree is trained by use of residuals between predicted values of the first regression tree and true values (weighted averages of the 4 feature points extracted from each sample picture) of the part of feature points, and so on, when predicted values of an Nth trained tree and the true values of the part of feature points are close to zero, all regression trees of the ERT algorithm are obtained, the eye mean shape about the faces is obtained according to these regression trees and a model file and the sample library are stored in the memory. Since each sample for training the model is marked with the 6 orbit feature points and the 1 eyeball feature point, the trained eye mean shape for the faces may be configured to recognize the 6 orbit feature points and 1 eyeball feature point from the facial image.

After the real-time facial image is acquired and the trained eye mean shape for faces is called from the memory, the real-time facial image is aligned with the eye mean shape and then the real-time facial image is searched for 6 orbit feature points and 1 eyeball feature point matched with 6 orbit feature points and 1 eyeball feature point of the eye mean shape by use of a feature extraction algorithm. In the embodiment, the feature extraction algorithm is a SIFT algorithm. According to the SIFT algorithm, local features of each orbit feature point and eyeball feature point are extracted from the eye mean shape, an orbit feature point and an eyeball feature point are selected as a reference feature point, and the real-time facial image is searched for a feature point with a local feature the same as or similar to that of the reference feature point (for example, a difference value of the local features of the two feature points is within a preset range). According to this principle, all of the orbit feature points and the eyeball feature points are found from the real-time facial image. In another embodiment, the feature extraction algorithm may also be a SURF algorithm, an LBP algorithm, a HOG algorithm and the like.

In S30, a movement direction and movement distance of an eyeball in the real-time facial image are calculated according to x and y coordinates of the $n_1$ orbit feature points and $n_2$ eyeball feature points in the real-time facial image.

Figure 4:
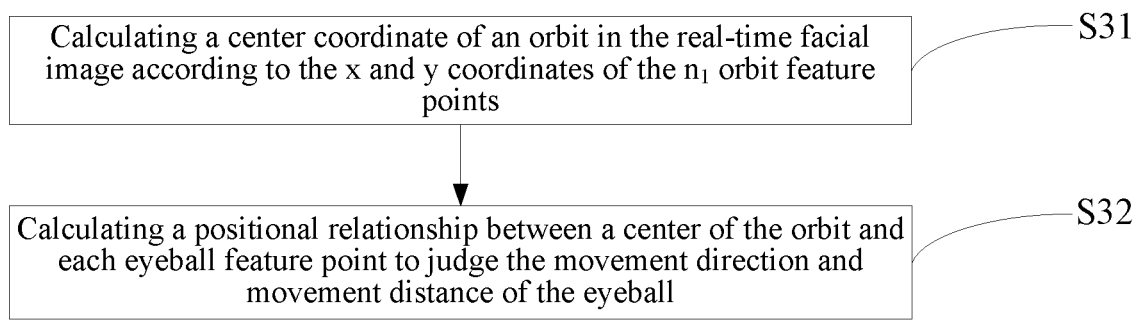
FIG. 4 is a detailed flowchart of S30 of an eyeball movement capturing method according to the application.

FIG. 4 is a detailed flowchart of S30 in an eyeball movement capturing method according to the application. Specifically, S30 includes the following steps.

In S31, a center coordinate of an orbit in the real-time facial image is calculated according to the x and y coordinates of the $n_1$ orbit feature points.

In S32, a positional relationship between a center of the orbit and each eyeball feature point is calculated to judge the movement direction and movement distance of the eyeball.

If there are 6 orbit feature points and 1 eyeball feature point in the eye feature points recognized from the real-time facial image, $(x_1, y_1)$, $(x_2, y_2)$, $(x_3, y_3)$, $(x_4, y_4)$, $(x_5, y_5)$ and $(x_6, y_6)$ being coordinates of the 6 orbit feature points respectively and $(x_7, y_7)$ being a coordinate of the eyeball feature point, calculation formulas for the center coordinate (X, Y) of the orbit in the real-time facial image are as follows:

$$centerX=(x_1+x_2+x_3+x_4+x_5+x_6)/6, \text{ and}$$

$$centerY=(y_1+y_2+y_3+y_4+y_5+y_6)/6.$$

By use of the center coordinate (X, Y) of the orbit and the coordinate $(x_7, y_7)$ of the eyeball feature point, the positional relationship therebetween is calculated and the movement direction and movement distance of the eyeball are judged through the following calculation formulae:

$$\Delta x=x_7-centerX \text{ and } \Delta y=y_7-centerY,$$

where values of $\Delta x$ and $\Delta y$ represent the movement distance of the eyeball in a certain direction (left-right and top-bottom).

For example, if $\Delta x$ is larger than 0, it is indicated that the eyeball moves leftwards and, if $\Delta x$ is smaller than 0, it is indicated that the eyeball moves rightwards; and if $\Delta y$ is larger than 0, it is indicated that the eyeball moves upwards and, if $\Delta y$ is smaller than 0, it is indicated that the eyeball moves downwards.

Similarly, when $n_2>1$, that is, there are multiple eyeball feature points in the eye mean shape, the multiple eyeball feature points may be recognized from the real-time facial image, then a mean value of the x and y coordinates of the multiple eyeball feature points is taken as a center coordinate of the eyeball and a difference value with the center coordinate of the orbit is calculated.

According to the eyeball movement capturing method disclosed in the embodiment, the orbit feature points and eyeball feature points in the real-time facial image are recognized by use of the eye mean shape and movement information of the eyeball in the real-time facial image is calculated according to the coordinates of the orbit feature points and the eyeball feature points to implement real-time capturing of an eyeball movement.

Moreover, an embodiment of the application also discloses a computer-readable storage medium, which includes an eyeball movement capturing program, the eyeball movement capturing program being executed by a processor to implement the following operations:

a real-time facial image acquisition step: a real-time image shot by the photographic device is acquired and a real-time facial image is extracted from the real-time image by use of a face recognition algorithm;

a feature point recognition step: the real-time facial image is input into a pretrained eye mean shape and $n_1$ orbit feature points and $n_2$ eyeball feature points representative of an eye position in the real-time facial image are recognized by use of the eye mean shape; and an eyeball position calculation step: a movement direction and movement distance of an eyeball in the real-time facial image are calculated according to x and y coordinates of the $n_1$ orbit feature points and $n_2$ eyeball feature points in the real-time facial image.

Optionally, the eyeball position calculation step includes that:

a center coordinate of an orbit in the real-time facial image is calculated according to the x and y coordinates of the $n_1$ orbit feature points; and a positional relationship between a center of the orbit and each eyeball feature point is calculated to judge the movement direction and movement distance of the eyeball.

Optionally, the feature point recognition step further includes that:

the real-time facial image is aligned with the eye mean shape and the real-time facial image is searched for the $n_1$ orbit feature points and $n_2$ eyeball feature points matched with $n_1$ orbit feature points and $n_2$ eyeball feature points of the eye mean shape by use of a feature extraction algorithm.

Optionally, the facial feature recognition model is an ERT algorithm and is represented by a formula as follows:

$$\hat{S}^{t+1} = \hat{S}^t + \tau_t(I, \hat{S}^t),$$

where t represents a concatenation sequence number, $\tau_t(\cdot,\cdot)$ represents a regressor of a present stage and S(t) is a shape estimate of a present model; each regressor $\tau_t(\cdot,\cdot)$ predicts an increment $\tau_t(I,\hat{S}^t)$ according to an input present image I and S(t); and in a model training process, part of feature points of all sample pictures are extracted to train a first regression tree, a second tree is trained by use of residuals between predicted values of the first regression tree and true values of the part of feature points, and so on, when predicted values of an Nth trained tree and the true values of the part of feature points are close to zero, all regression trees of the ERT algorithm are obtained, and the eye mean shape for the faces is obtained according to these regression trees.

Specific implementation modes of the computer-readable storage medium of the application are substantially the same as the specific implementation modes of the eyeball movement capturing method and will not be elaborated herein.

It is to be noted that terms "include" and "contain" or any other variant thereof in the disclosure are intended to cover nonexclusive inclusions, so that a process, device, object or method including a series of elements not only includes those elements but also includes other elements which are not listed clearly or further includes elements intrinsic to the process, the device, the object or the method. Under the condition of no more restrictions, an element defined by a statement "including a/an . . . " does not exclude existence of the same other element in a process, device, object or method including the element.

The foregoing numbering of the embodiments of the application is intended for description only, and is not indicative of the pros and cons of these embodiments. By the description of the foregoing embodiments, it will be evident to those skilled in the art that the methods of the embodiments can be implemented by means of software plus the necessary general-purpose hardware platform; and they can of course be implemented by hardware, but in many cases the former will be more advantageous. Based on such an understanding, the essential technical solution of the application, or the portion that contributes to the prior art may be embodied as software products. Computer software products can be stored in a storage medium (e.g., a read-only memory (ROM)/random access memory (RAM), a magnetic disk, an optical disc), including multiple instructions that, when executed, can cause a piece of terminal equipment (e.g., a mobile phone, a computer, a server, a network device), to execute the methods described in the various embodiments of the application.

The above is only the preferred embodiment of the application and therefore is not intended as limiting the protection scope of the application. Any equivalent configurational or flow transformations that are made taking advantage of the application and that are used directly or indirectly in any other related technical field shall all fall in the scope of protection of the application.

What is claimed is:

1. An electronic device, comprising: a memory, a processor and a photographic device, the memory comprising an eyeball movement capturing program and the eyeball movement capturing program being executed by the processor to implement the following steps of:
    a real-time facial image acquisition step: acquiring a real-time image shot by the photographic device and extracting a real-time facial image from the real-time image by use of a face recognition algorithm;
    a feature point recognition step: inputting the real-time facial image into a pretrained eye mean shape and recognizing $n_1$ orbit feature points and $n_2$ eyeball feature points representative of an eye position in the real-time facial image by use of the eye mean shape; and
    an eyeball position calculation step: calculating a movement direction and movement distance of an eyeball in the real-time facial image according to x and y coordinates of the $n_1$ orbit feature points and $n_2$ eyeball feature points in the real-time facial image, wherein the eyeball position calculation step comprises:
    calculating a center coordinate of an orbit in the real-time facial image according to the x and y coordinates of the $n_1$ orbit feature points; and
    calculating a positional relationship between a center of the orbit and each eyeball feature point to judge the movement direction and movement distance of the eyeball.

2. The electronic device of claim 1, wherein the feature point recognition step further comprises:
    aligning the real-time facial image and the eye mean shape and searching the real-time facial image for the $n_1$ orbit feature points and $n_2$ eyeball feature points matched with $n_1$ orbit feature points and $n_2$ eyeball feature points of the eye mean shape by use of a feature extraction algorithm.

3. The electronic device of claim 2, wherein the feature extraction algorithm comprises a scale-invariant feature transform (SIFT) algorithm, a speeded up robust features (SURF) algorithm, a local binary patterns (LBP) algorithm and a histogram of oriented gradients (HOG) algorithm.

4. The electronic device of claim 2, wherein training steps for the eye mean shape comprise:
    a feature vector sample extraction step: establishing a sample library with n facial images and marking $n_1$ orbit feature points and $n_2$ eyeball feature points in each facial image in the sample library, the $(n_1+n_2)$ feature points in each facial image forming a shape feature vector S to obtain n shape feature vectors S of an eye; and
    a model training step: training a facial feature recognition model by use of the n shape feature vectors S to obtain the eye mean shape about faces.

5. The electronic device of claim 4, wherein the facial feature recognition model is an ensemble of regression trees (ERT) algorithm and is represented by a formula as follows:

$$\hat{S}^{t+1} = \hat{S}^t + \tau_t(I, \hat{S}^t),$$

where t represents a concatenation sequence number, $\tau_t(\cdot,\cdot)$ represents a regressor of a present stage and S(t) is a shape estimate of a present model; each regressor $\tau_t(\cdot,\cdot)$ predicts an increment $\tau_t(I, \hat{S}^t)$ according to an input present image I and S (t); and in a model training process, part of feature points of all sample pictures are extracted to train a first regression tree, a second tree is trained by use of residuals between predicted values of the first regression tree and true values of the part of feature points, and so on, when predicted values of an Nth trained tree and the true values of the part of feature points are close to zero, all regression trees of the ERT algorithm are obtained, and the eye mean shape for the faces is obtained according to these regression trees.

6. The electronic device of claim 1, wherein the face recognition algorithm is one of a geometric-feature-based method, a local feature analysis method, an eigenface method, an elastic-model-based method and a neural network method.

7. An eyeball movement capturing method, applied to an electronic device and comprising:
a real-time facial image acquisition step: acquiring a real-time image shot by a photographic device and extracting a real-time facial image from the real-time image by use of a face recognition algorithm;
a feature point recognition step: inputting the real-time facial image into a pretrained eye mean shape and recognizing $n_1$ orbit feature points and $n_2$ eyeball feature points representative of an eye position in the real-time facial image by use of the eye mean shape; and
an eyeball position calculation step: calculating a movement direction and movement distance of an eyeball in the real-time facial image according to x and y coordinates of the $n_1$ orbit feature points and $n_2$ eyeball feature points in the real-time facial image, wherein the eyeball position calculation step comprises:
calculating a center coordinate of an orbit in the real-time facial image according to the x and y coordinates of the $n_1$ orbit feature points; and
calculating a positional relationship between a center of the orbit and each eyeball feature point to judge the movement direction and movement distance of the eyeball.

8. The eyeball movement capturing method of claim 7, wherein the feature point recognition step further comprises:
aligning the real-time facial image and the eye mean shape and searching the real-time facial image for the $n_1$ orbit feature points and $n_2$ eyeball feature points matched with $n_1$ orbit feature points and $n_2$ eyeball feature points of the eye mean shape by use of a feature extraction algorithm.

9. The eyeball movement capturing method of claim 8, wherein the feature extraction algorithm comprises a scale-invariant feature transform (SIFT) algorithm, a speeded up robust features (SURF) algorithm, a local binary patterns (LBP) algorithm and a histogram of oriented gradients (HOG) algorithm.

10. The eyeball movement capturing method of claim 8, wherein training steps for the eye mean shape comprise:
a feature vector sample extraction step: establishing a sample library with n facial images and marking $n_1$ orbit feature points and $n_2$ eyeball feature points in each facial image in the sample library, the $(n_1+n_2)$ feature points in each facial image forming a shape feature vector S to obtain n shape feature vectors S of an eye; and
a model training step: training a facial feature recognition model by use of the n shape feature vectors S to obtain the eye mean shape about faces.

11. The eyeball movement capturing method of claim 10, wherein the facial feature recognition model is an ensemble of regression trees (ERT) algorithm and is represented by a formula as follows:

$$\hat{S}^{t+1}=\hat{S}^t+\tau_t(I,\hat{S}^t),$$

where t represents a concatenation sequence number, $\tau_t(\cdot,\cdot)$ represents a regressor of a present stage and S(t) is a shape estimate of a present model; each regressor $\tau_t(\cdot,\cdot)$ predicts an increment $\tau_t(I,\hat{S}^t)$ according to an input present image I and S(t); and in a model training process, part of feature points of all sample pictures are extracted to train a first regression tree, a second tree is trained by use of residuals between predicted values of the first regression tree and true values of the part of feature points, and so on, when predicted values of an Nth trained tree and the true values of the part of feature points are close to zero, all regression trees of the ERT algorithm are obtained, and the eye mean shape for the faces is obtained according to these regression trees.

12. The eyeball movement capturing method of claim 7, wherein the face recognition algorithm is one of a geometric-feature-based method, a local feature analysis method, an eigenface method, an elastic-model-based method and a neural network method.

13. A non-transitory computer-readable storage medium, comprising an eyeball movement capturing program, the eyeball movement capturing program being executed by a processor to implement the following steps of:
a real-time facial image acquisition step: acquiring a real-time image shot by a photographic device and extracting a real-time facial image from the real-time image by use of a face recognition algorithm;
a feature point recognition step: inputting the real-time facial image into a pretrained eye mean shape and recognizing $n_1$ orbit feature points and $n_2$ eyeball feature points representative of an eye position in the real-time facial image by use of the eye mean shape; and
an eyeball position calculation step: calculating a movement direction and movement distance of an eyeball in the real-time facial image according to x and y coordinates of the $n_1$ orbit feature points and $n_2$ eyeball feature points in the real-time facial image, wherein the eyeball position calculation step comprises:
calculating a center coordinate of an orbit in the real-time facial image according to the x and y coordinates of the $n_1$ orbit feature points; and
calculating a positional relationship between a center of the orbit and each eyeball feature point to judge the movement direction and movement distance of the eyeball.

14. The non-transitory computer-readable storage medium of claim 13, wherein the feature point recognition step further comprises:
aligning the real-time facial image and the eye mean shape and searching the real-time facial image for the $n_1$ orbit feature points and $n_2$ eyeball feature points matched with $n_1$ orbit feature points and $n_2$ eyeball feature points of the eye mean shape by use of a feature extraction algorithm.

15. The non-transitory computer-readable storage medium of claim 14, wherein the feature extraction algorithm comprises a scale-invariant feature transform (SIFT) algorithm, a speeded up robust features (SURF) algorithm, a local binary patterns (LBP) algorithm and a histogram of oriented gradients (HOG) algorithm.

16. The non-transitory computer-readable storage medium of claim 14, wherein training steps for the eye mean shape comprise:
a feature vector sample extraction step: establishing a sample library with n facial images and marking $n_1$ orbit feature points and $n_2$ eyeball feature points in each facial image in the sample library, the $(n_1+n_2)$ feature points in each facial image forming a shape feature vector S to obtain n shape feature vectors S of an eye; and a model training step: training a facial feature recognition model by use of the n shape feature vectors S to obtain the eye mean shape about faces.

17. The non-transitory computer-readable storage medium of claim 16, wherein the facial feature recognition model is an ensemble of regression trees (ERT) algorithm and is represented by a formula as follows:

$$\hat{S}^{t+1} = \hat{S}^t + \tau_t(I, \hat{S}^t),$$

where t represents a concatenation sequence number, $\tau_t(\cdot,\cdot)$ represents a regressor of a present stage and S(t) is a shape estimate of a present model; each regressor $\tau_t(\cdot,\cdot)$ predicts an increment $\tau_t(I,\hat{S}^t)$ according to an input present image I and S (t); and in a model training process, part of feature points of all sample pictures are extracted to train a first regression tree, a second tree is trained by use of residuals between predicted values of the first regression tree and true values of the part of feature points, and so on, when predicted values of an Nth trained tree and the true values of the part of feature points are close to zero, all regression trees of the ERT algorithm are obtained, and the eye mean shape for the faces is obtained according to these regression trees.

* * * * *